(12) United States Patent
Bacher et al.

(10) Patent No.: US 8,178,489 B2
(45) Date of Patent: May 15, 2012

US008178489B2

(54) FORMULATION FOR AVIPTADIL

(75) Inventors: Gerald Bacher, Germering (DE);
Dorian Bevec, Germering (DE)

(73) Assignee: MondoBiotech AG, Stans (CH)

( * ) Notice: Subject to any disclaimer, the term of this patent is extended or adjusted under 35 U.S.C. 154(b) by 1214 days.

(21) Appl. No.: 11/817,867

(22) PCT Filed: Mar. 7, 2006

(86) PCT No.: PCT/EP2006/002084
§ 371 (c)(1),
(2), (4) Date: Sep. 5, 2007

(87) PCT Pub. No.: WO2006/094764

PCT Pub. Date: Sep. 14, 2006

(65) Prior Publication Data
US 2008/0161237 A1 Jul. 3, 2008

Related U.S. Application Data

(60) Provisional application No. 60/662,821, filed on Mar. 18, 2005.

(30) Foreign Application Priority Data

Mar. 7, 2005 (DE) .......................... 10 2005 010 415

(51) Int. Cl.
| A61K 38/00 | (2006.01) |
|---|---|
| A61K 38/36 | (2006.01) |
| A61P 11/00 | (2006.01) |
| A61P 9/12 | (2006.01) |
| A61P 9/00 | (2006.01) |
| A61P 25/28 | (2006.01) |
| A61P 25/02 | (2006.01) |

(52) U.S. Cl. ...... 514/1.5; 514/14.9; 514/15.7; 514/16.4; 514/17.8; 514/18.2

(58) Field of Classification Search ........................ None
See application file for complete search history.

(56) References Cited

U.S. PATENT DOCUMENTS

| 3,898,329 | A |   | 8/1975  | Said et al. ................... 424/177 |
|---|---|---|---|---|
| 4,016,258 | A |   | 4/1977  | Said et al. |
| 4,237,046 | A |   | 12/1980 | Bodanszky ............... 260/112.5 |
| 4,783,441 | A | * | 11/1988 | Thurow .......................... 514/6.3 |
| 5,236,904 | A |   | 8/1993  | Gerstenberg et al. |
| 5,428,015 | A |   | 6/1995  | Kurono et al. |
| 5,447,912 | A | * | 9/1995  | Gerstenberg et al. .......... 514/9.7 |
| 5,681,816 | A |   | 10/1997 | Korman |
| 5,736,509 | A | * | 4/1998  | Balaji et al. ................. 514/16.1 |
| 5,958,881 | A |   | 9/1999  | Korman |
| 7,459,441 | B2 | * | 12/2008 | Minagawa et al. ............. 514/1.1 |
| 2004/0259796 | A1 | * | 12/2004 | Minagawa et al. ............. 514/13 |

FOREIGN PATENT DOCUMENTS

| EP | 1 571 155 A1 |   | 9/2005 |
|---|---|---|---|
| WO | WO 95/05188 A1 |   | 2/1995 |
| WO | WO 01/34088 |   | 5/2001 |
| WO | WO 03/039577 | * | 5/2003 |
| WO | WO 2004/048401 A1 |   | 6/2004 |

OTHER PUBLICATIONS

Buffers (From Ruzzin, 1999, Plant Microtechnique and Microscopy, accessed online at http://microscopy.berkeley.edu/Resources/instruction/buffers.html, Jan. 29, 2011, 5 pages.*
Kishi et al. VIP- and PACAP-mediated nonadrenergic, noncholinergic inhibition in longitudinal muscle of rat distal colon: involvement of activation of charybdotoxin- and apamin-sensitive K+ channels. British Journal of Pharmacology, 1996, vol. 119, pp. 623-630.*
Okada et al. Sites of action of brain-gut peptides in cultured neurons of rat brainstem. Brain Research, 1985, Vo. 348, pp. 175-179.*
Fournier et al. Synthesis, Conformational Studies and Biological Activities of VIP and Related Fragments. 1984. Peptides. vol. 5, pp. 169-177.*
Keijzers. Aviptadil (Senatek) Current Opin Investig Drugs, 2001. vol. 2, Nol. 4, pp. 545-549.*
Christine Dupes et al., "Brain delivery of vasoactive intestinal peptide (VIP) following nasal administration to rats" International Journal of Pharmaceutics, vol. 255, Apr. 2003, pp. 87-97.
Wei Xu et al., "Progress of Research of Vasoactive Intestinal Peptide" Pharmaceutical Biotechnology, vol. 9, No. 6, 2002, pp. 364-368.
Chinese First Examination Report of China Application No. 2006800072361, dated Nov. 27, 2009.
Paulou T.A. et al., "Infusion of Vasoactive Intestinal Peptide Improves Hemodynamics in Pimary Pulmonary Hypertension" American Review of Respiratory Disease, vol. 14, 1993, p. A536 Suppl. S.
I.M. Keith, "The Role of Endogenous Lung Neuropeptides in Regulation of the Pulmonary Circulation" Physiological Research, vol. 49(5), 2000, pp. 519-537.
Iwanaga T. et al., "Vasoactive Intestinal Peptide VIP Protects Against Acid-Induced Acute Lung Injury in Isolated Perfused Rat Lungs" Japanese Journal of Thoracic Diseases, 1989, vol. 27(7), pp. 789-795.
Junya Kawasaki et al., "The mechanisms of the relaxation induced by vasoactive intestinal peptide in the porcine coronary artery" British Journal of Pharmacology (1997), vol. 121, pp. 977-985.
Kaname Maruno et al., "VIP inhibits basal and histamine-stimulated proliferation of human airway smooth muscle cells" American journal of Physiology, 1995, vol. 268(6), pp. L1047-L1051.
Oleksandr Platoshyn et al., "Sustained membrane depolarization and pulmonary artery smooth muscle cell proliferation" American Journal of Physiology, 2000, vol. 279(5), pp. C1540-C1549.
International Search Report and Written Opinion mailed Jul. 4, 2006, in PCT/EP2006/002084, 15 pages.
Ashok et al., "Effects of peptide molecular mass and PEG chain length on the vasoreactivity of VIP and PACAP1-38 in pegylated phospholipid micelles," Peptides, Aug. 2004, 25(8):1253-1258.
Dufes et al., "Glucose-targeted niosomes deliver vasoactive intestinal peptide (VIP) to the brain," International Journal of Pharmaceutics, Nov. 5, 2004, 285(1-2):77-85.
Gololobov et al., "Stabilization of vasoactive intestinal peptide by lipids," Journal of Pharmacology and Experimental Therapeutics, 1998, 285(2):753-758.

(Continued)

*Primary Examiner* — Marcela M Cordero Garcia
(74) *Attorney, Agent, or Firm* — Meyertons, Hood, Kivlin, Kowert & Goetzel, P.C.; Eric B. Meyertons

(57) ABSTRACT

The present invention relates to pharmaceutical formulations of Aviptadil and its derivatives. The stability of the Aviptadil formulation was shown to be improved by a formulation having a defined concentration of Aviptadil prepared in a buffer having a defined pH range.

20 Claims, 1 Drawing Sheet

OTHER PUBLICATIONS

Gozes et al., "VIP and drug design," Current Pharmaceutical Design, 2003, 9(6):483-494.

Mody et al., "Spontaneous hydrolysis of vasoactive intestinal peptide in neutral aqueous solution," International Journal of Peptide and Protein Research, Nov. 1, 1994, 44(5):441-447.

Séjourné et al., "Development of a novel bioactive formulation of vasoactive intestinal peptide in sterically stabilized liposomes," Pharmaceutical Research, Mar. 1997, 14(3):362-365.

Bachem AG, Aviptadil product data sheet, Sep. 7, 2011.

* cited by examiner

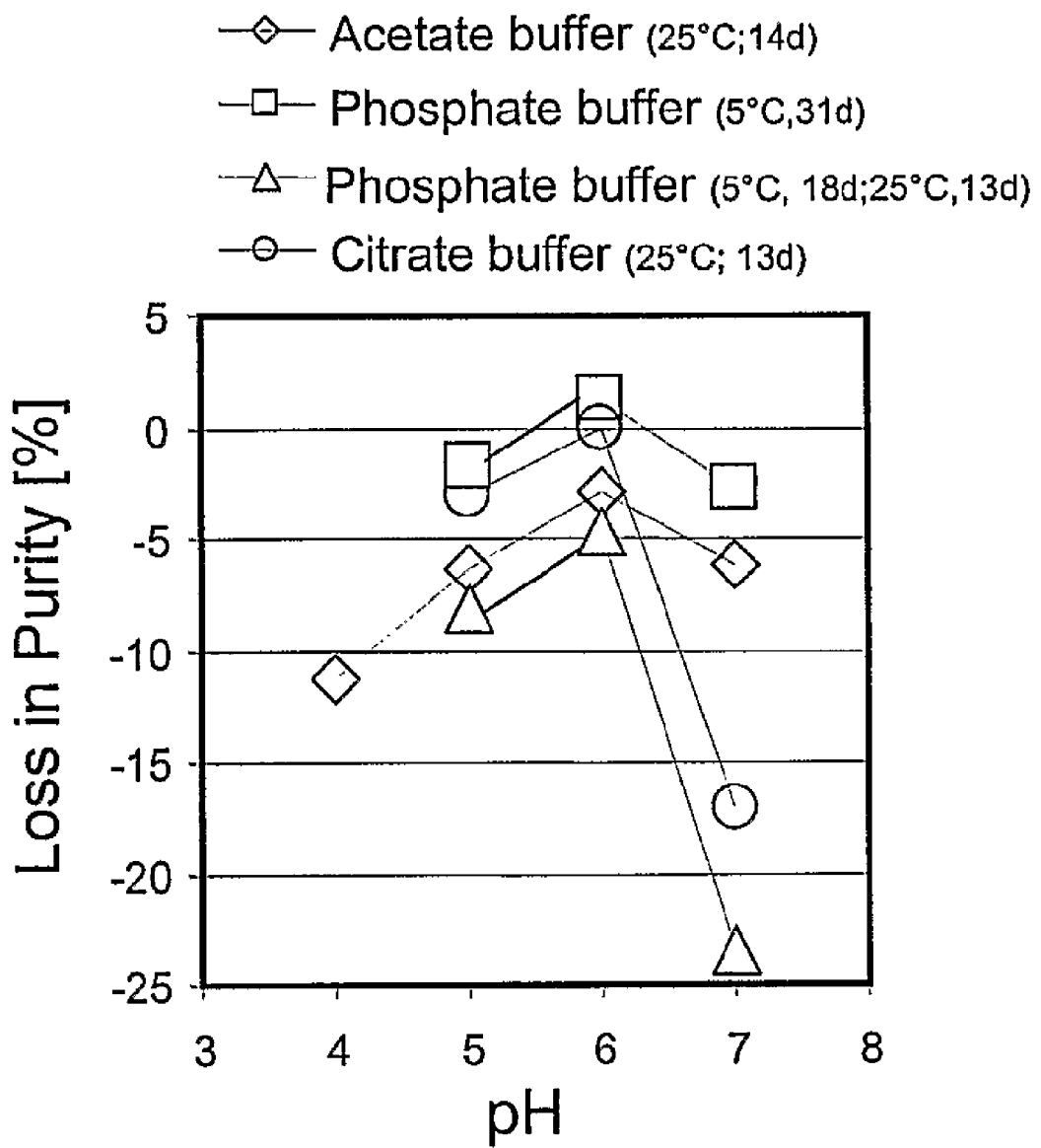

SEQUENCE LISTING

```
<160> NUMBER OF SEQ ID NOS: 2

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

FORMULATION FOR AVIPTADIL

FIELD OF INVENTION

The present invention relates to pharmaceutical formulations of Aviptadil and its derivatives.

BACKGROUND OF THE INVENTION

Aviptadil (VIP, vasoactive intestinal peptide) has been used in the United States and in European countries for more than 2 decades in controlled experiments involving humans and animals. Aviptadil for injection is approved in combination with phentolamine for treatment of erectile dysfunction in the United Kingdom, Denmark and New Zealand. Pharmacology and toxicology of the endogenous peptide Aviptadil have been described in a large number of peer-reviewed publications since its discovery in the early 1970's.

Endogenous Aviptadil, also called vasoactive intestinal peptide (VIP), is a peptide which consists of 28 amino acids and which has following amino acid sequence (from the N- to the C-terminus): His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO: 1).

Conformational analysis of Aviptadil by two-dimensional NMR and circular dichroism spectroscopy has shown an initial disordered N-terminus sequence of eight amino acid residues with two beta-turns, followed by two helical segments at residues 7-15 and 19-27 connected by a region of undefined structure that confers mobility to the peptide molecule. Endogenous Aviptadil is synthesized from a precursor molecule which contains 170 amino acids and is processed to its biologically active form via a signal peptidase in the endoplasmic reticulum and finally cleaved by prohormone convertases and by carboxypeptidase-B like enzymes to Aviptadil.

Aviptadil was first isolated from the intestine. Several years later Aviptadil was identified in the central and peripheral nervous system, and has since been recognized as a widely distributed neuropeptide, acting as a neurotransmitter or neuromodulator in many organs and tissues, including heart, lung, thyroid gland, kidney, immune system, urinary tract and genital organs.

The widespread distribution of Aviptadil in mammals, including humans, is correlated with its involvement in a wide variety of physiological activities including smooth muscle relaxation which leads to systemic vasodilation, increased cardiac output, bronchodilation, and regulation of arterial pulmonary blood pressure, gastrointestinal smooth muscle cell relaxation and some differential effects on secretory processes in the gastrointestinal tract and gastric motility, hyperglycemia, inhibition of smooth muscle cell proliferation, hormonal regulation, analgesia, hyperthermia, neurotropic effects, learning and behavior, and bone metabolism.

Aviptadil is acid-labile and thermo-labile in isotonic salt solutions between 30° C. to 60° C.

Historically, Aviptadil was used over a long period of time in various human clinical trials administered either via the intravenous, intracavernous, or inhalative route. The current state of the art method for the preparation of a clinically applicable Aviptadil as a single medicament comprises the synthetic generation of the Aviptadil substance as a white powder, which is subsequently reconstituted in 0.9% sodium chloride solution (isotonic solution) at a concentration of 0.033 mg/mL. In another composition with phentolamine, Aviptadil is dissolved in a phosphate buffer (pH values between 2 and 4.5) containing ethylene diaminetetraacetate (EDTA) as stabilizer (EP0493485; U.S. Pat. No. 5,236,904; U.S. Pat. No. 5,447,912; WO9505188).

Many factors affect the stability of a pharmaceutical product, including the chemical reactivity of the active ingredient(s), the potential interaction between active and inactive ingredients, the manufacturing process, the dosage form, the container closure system, and the environmental conditions encountered during shipment, storage, handling and length of time between manufacture and usage. Pharmaceutical product stability is determined by the chemical stability as well as the physical stability of the formulation. Physical factors including heat and light may initiate or accelerate chemical reactions.

Optimal physical stability of a formulation is very important for at least three primary reasons. First, a pharmaceutical product must appear fresh, elegant and professional when it is administered to a patient. Any change in physical appearance such as color changes of haziness can cause a patient or consumer to have less confidence in the product. Second, because some products are dispensed in multiple dose containers, uniformity of dose content of the active ingredient over time must be assured. A cloudy solution or a broken emulsion can lead to a non-uniform dosage pattern. Third, the active ingredient must be available to the patient throughout the expected shelf life of the preparation. A breakdown of the product to inactive or otherwise undesired forms can lead to non-availability of the medicament to the patient.

Stability of a pharmaceutical product, then, may be defined as the capability of a particular formulation to remain within its physical, chemical, microbiological, therapeutic and toxicological specifications.

A stable solution retains its original clarity, color, and odor throughout its shelf life. Retention of clarity of a solution is a main concern in maintaining physical stability. Solutions should remain clear over a relatively wide temperature range, such as 4° C. to about 37° C. At the lower range an ingredient may precipitate due to a lower solubility at that temperature, while at higher temperatures homogeneity may be destroyed by extractables from the glass containers or rubber closures. Thus, solutions of active pharmaceutical ingredients must be able to handle cycling temperature conditions. Similarly, a formulation should retain its color throughout this temperature range, and its odor should be stably maintained.

Small peptides are typically unstable and are susceptible to degradation in aqueous solution. In this regard, once Aviptadil has less than 90% of its labeled potency, it is no longer considered to be suitable for administration to a patient.

Various types of sugars, surfactants, amino acids and fatty acids, used singly or in combination, have been used in efforts to stabilize protein and peptide products against degradation. Wang and Hanson, J. Parenteral Science and Technology Supplement, 1988, Technical Report No. 10 describe parenteral formulations of proteins and peptides. Examples of excipients such as buffers, preservatives, isotonic agents, and surfactants are described by Manning et al., 6 Pharmaceutical Research, 1989, by Wang and Kowak, 34 J. Parenteral Drug Association 452, 1980, and Avis et al., Pharmaceutical Dosage Forms: Parenteral Medications, Vol. 1, 1992.

It is understood that the development of a suitable pharmaceutical formulation for administration to a subject is complex. A need exists in the art for pharmaceutical formulations of Aviptadil designed to provide a single or multiple doses having substantial stability when refrigerated and at room temperature. Further, a need exists in the art for a liquid pharmaceutical formulation packaged with an appropriate container/closure system that also minimizes the physical and chemical degradation of such peptides.

It is an object of current invention to provide an effective, more stable, liquid Aviptadil formulation for the manufacture of a medicament suitable for inhalative or injectable medical administration for patients in need thereof. In another embodiment, it is an object of the current invention to provide a liquid Aviptadil formulation that allows long term storage of a medicament containing Aviptadil, thereby facilitating simplified storage and shipment conditions. In yet another embodiment it is an object of the current invention to provide a liquid pharmaceutical composition containing a pharmacologically active amount of Aviptadil and a pharmacologically active amount of the following peptides: Cyclo D-Asp-Pro-D-Val-Leu-D-Trp, or Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Lys-Val-Leu-Arg-Arg-His (SEQ ID NO: 2).

DETAILED DESCRIPTION OF THE INVENTION

An aspect of the invention described herein features a method for formulating Aviptadil in a stable, biologically active and safe pharmaceutical composition for administration to a patient.

Peptide drugs undergo physical and chemical degradation in solution, and lose their biological activity. The dosage form reported in this invention minimizes the chemical degradation of Aviptadil e.g. peptide bond hydrolysis and maintains the peptide in a biologically active form for more than 1 year when stored at 2 to 8° C. This dosage form is also well tolerated by animals and humans.

An aspect of the invention herein describes the production of a liquid pharmaceutical formulation which comprises approximately 0.001% to 1.0% (w/v) of Aviptadil. Surprisingly, we found that formulations containing higher concentrations of from 0.0066, preferably from 0.01, more preferably from 0.05 and still more preferably from 0.1 to 1.0% (w/v) of Aviptadil are substantially more stable.

The stability of the peptide formulation of the present invention is enhanced by maintaining the pH of the formulation in the range of approximately 4.8 to 6.7. Preferably, the pH of the formulation is maintained in the range of 5.0 to 6.4, more preferably 5.5 to 6.3 and most preferably 5.7 to 6.1. An especially preferred pH range 5.9 to 6.1. It has been shown that if the pH of the pharmaceutical formulation exceeds 6.7 or drops below 4.8 chemical degradation of the peptide is enhanced and shelf life of the peptide is reduced.

The term buffer, buffer system, buffer solution and buffered solution, when used with reference to hydrogen-ion concentration or pH, refers to the ability of a system, particularly an aqueous solution, to resist a change of pH on adding acid or alkali, or on dilution with a solvent. Characteristics of buffered solutions, which undergo small changes of pH on addition of acid and base, in the presence either of a weak acid and a salt of the weak acid, or a weak base and a salt of the weak base. An example of the former system is citric acid and sodium citrate. The change of pH is slight as the amount of hydronium or hydroxyl ion added does not exceed the capacity of the buffer system to neutralize it.

To maintain the pH within 4.8 to 6.7 preferably buffer systems are used which have an appropriate buffering capacity. The buffering capacity of the buffer is highest at its pKa (association constant) value because both undissociated and dissociated forms (acid and conjugate base) are present in equal concentration. Upon addition of acid, it will be immediately neutralized by concentration of conjugated base and if alkali is added, concentration of acid will be plentiful to neutralize it. This optimal buffering occurs when the desired pH is within approximately 1 pH unit from the pKa value for the buffering system. Thus, all buffer systems with a pKa value within the range of 3.8 to 7.7 is preferably used to stabilize Aviptadil. Preferably the pKa of the buffers is in the range of 4.0 to 7.4, preferably 4.5 to 7.3, more preferably in the range of 4.7-7.1 and especially preferred are buffers with a pKa in the range of 4.9 to 7.1.

The buffer systems can be selected from the group consisting of formate (pKa=3.75), lactate (pKa=3.86), benzoic acid (pKa=4.2) oxalate (pKa=4.29), fumarate (pKa=4.38), aniline (pKa=4.63), acetate buffer (pKa=4.76), citrate buffer (pKa2=4.76, pKa3=6.4), glutamate buffer (pKa=4.3), phosphate buffer (pKa=7.20), succinate (pka1=4.93; pKa2=5.62), pyridine (pKa=5.23), phthalate (pKa=5.41); histidine (pKa=6.04), MES (2-(N-morpholino)ethanesulphonic acid; pKa=6.15); maleic acid (pKa=6.26); cacodylate (dimethylarsinate, pKa=6.27), carbonic acid (pKa=6.35), ADA (N-(2-acetamido)imino-diacetic acid (pKa=6.62); PIPES (4-piperazinebis-(ethanesulfonic acid; BIS-TRIS-propane (1,3-bis[tris(hydroxymethyl)methylamino]-propane), pKa=6.80), ethylendiamine (pKa=6.85), ACES 2-[(2-amino-2-oxoethyl)amino]ethanesulphonic acid; pKa=6.9), imidazole (pKa=6.95), MOPS (3-(N-morphin)-propansulfonic acid; pKa=7.20), diethylmalonic acid (pKa=7.2), TES (2-[tris (hydroxymethyl)methyl]amino ethanesulphonic acid; pKa=7.50) and HEPES (N-2-hydroxylethylpiperazin-N'-2-ethansulfonic acid; pKa=7.55) buffers or other buffers having a pKa between 3.8 to 7.7 and capable of maintaining the pH of the formulation between 4.8 to 6.7.

Preferred is the group of carboxylic acid buffers such as acetate and carboxylic diacid buffers such as fumarate, tartrate and phthalate and carboxylic triacid buffers such as citrate. Another group of preferred buffers is represented by inorganic buffers such as sulfate, borate, carbonate, oxalate, calcium hydroxyde and phosphate buffers. Another group of preferred buffers are nitrogen containing buffers such as imidazole, diethylenediamine, piperazine.

Also preferred are sulfonic acid buffers such as TES, HEPES, ACES, PIPES, [(2-hydroxy-1,1-bis(hydroxymethyl)ethyl)amino]-1-propanesulfonic acid (TAPS), 4-(2-hydroxyethyl)piperazine-1-propanesulfonic acid (EPPS), 4-Morpholinepropanesulfonic acid (MOPS) and N,N-bis(2-hydroxyethyl)-2-aminoethanesulfonic acid (BES).

Another group of preferred buffers are glycine buffers such as glycine, glycyl-glycine, glycyl-glycyl-glycine, N,N-bis(2-hydroxyethyl)glycine and N-[2-hydroxy-1,1-bis(hydroxymethyl)ethyl]glycine (Tricine).

Preferred are also amino acid buffers such as glycine, tyrosine, glutamic acid, glutamate, aspartic acid, aspartate, barbiturate, 5,5-diethylbarbiturate, methionine, arginine, alanine, tryptophan, lysine, serine and histidine.

Also preferred are the following buffers:

| effective pH range | pKa 25° C. | buffer |
| --- | --- | --- |
| 2.7-4.2 | 3.40 | malate (pK1) |
| 3.0-4.5 | 3.75 | formate |
| 3.0-6.2 | 4.76 | citrate (pK2) |
| 3.2-5.2 | 4.21 | succinate (pK1) |
| 3.6-5.6 | 4.76 | acetate |
| 3.8-5.6 | 4.87 | propionate |
| 4.0-6.0 | 5.13 | malate (pK2) |
| 4.9-5.9 | 5.23 | pyridine |
| 5.0-6.0 | 5.33 | piperazine (pK1) |

| effective pH range | pKa 25° C. | buffer |
| --- | --- | --- |
| 5.0-7.4 | 6.27 | cacodylate |
| 5.5-6.5 | 5.64 | succinate (pK2) |
| 5.5-6.7 | 6.10 | MES |
| 5.5-7.2 | 6.40 | citrate (pK3) |
| 5.5-7.2 | 6.24 | maleate (pK2) |
| 5.5-7.4 | 1.70, 6.04, 9.09 | histidine |
| 5.8-7.2 | 6.46 | bis-tris |
| 5.8-8.0 | 7.20 | phosphate (pK2) |
| 6.0-12.0 | 9.50 | ethanolamine |
| 6.0-7.2 | 6.59 | ADA |
| 6.0-8.0 | 6.35 | carbonate (pK1) |
| 6.1-7.5 | 6.78 | ACES |
| 6.1-7.5 | 6.76 | PIPES |
| 6.2-7.6 | 6.87 | MOPSO |
| 6.2-7.8 | 6.95 | imidazole |
| 6.3-9.5 | 6.80, 9.00 | BIS-TRIS propane |
| 6.4-7.8 | 7.09 | BES |
| 6.5-7.9 | 7.14 | MOPS |
| 6.8-8.2 | 7.48 | HEPES |
| 6.8-8.2 | 7.40 | TES |
| 6.9-8.3 | 7.60 | MOBS |
| 7.0-8.2 | 7.52 | DIPSO |
| 7.0-8.2 | 7.61 | TAPSO |
| 7.0-8.3 | 7.76 | triethanolamine (TEA) |
| 7.0-9.0 | 0.91, 2.10, 6.70, 9.32 | pyrophosphate |
| 7.1-8.5 | 7.85 | HEPPSO |
| 7.2-8.5 | 7.78 | POPSO |

Preferred are the buffers having an effective pH range of from 2.7 to 8.5, more preferred of from 3.8 to 7.7, and of from 4.0 to 7.4, and most preferred of from 4.5-7.3 and especially preferred of from 5.0 to 7.0. The effective pH range for each buffer can be defined as pKa−1 to pKa+1, where Ka is the ionization constant for the weak acid in the buffer and pKa=−log K.

As cations for these buffers sodium, lithium, potassium, magnesium, calcium, tris(hydroxymethyl)aminomethane, trimethylammonium and ammonium are preferred.

Most preferred are buffers suitable for pharmaceutical use e.g. buffers suitable for administration to a patient such as acetate, carbonate, citrate, fumarate, glutamate, lactate, phosphate, phthalate, and succinate buffers. Particularly preferred examples of commonly used pharmaceutical buffers are acetate buffer, citrate buffer, glutamate buffer and phosphate buffer. Description of suitable pharmaceutical buffers can be found, for example, in "Remington's Pharmaceutical Sciences".

Also most preferred is the group of carboxylic acid buffers. The term "carboxylic acid buffers" as used herein shall refer to carboxylic mono acid buffers and carboxylic diacid buffers as well as carboxylic triacid buffers. Of course also combinations of buffers, especially of the buffers mentioned herein are useful for the present invention.

Some suitable pharmaceutical buffers, as disclosed in the examples, are a citrate buffer (preferably at a final formulation concentration of from about 20 to 200 mM, more preferably at a final concentration of from about 30 to 120 mM) or an acetate buffer (preferably at a final formulation concentration of about 20 to 200 mM) or a phosphate buffer (preferably at a final formulation concentration of about 20 to 200 mM).

Also in the present invention sodium chloride may be used to maintain the desired pH and thus act as the buffer component. The pH of an Aviptadil formulation prepared in 0.9% (w/v) sodium chloride solution was between 5.3 and 5.8.

The prior art formulation has the extremely acidic pH of 2-4.5. This highly acidic pH is vastly different from the approximately neutral physiological pH of blood and mammalian respiratory tract cells. The pH of the Aviptadil formulation of the present invention is preferably in the range of 4.8 to 6.7 and more preferably in the range of 5.0 to 6.4 and most preferably in the range of 5.5 to 6.3. Thus the pharmaceutical formulation of the present invention provides a medicament that reduces the occurrence of membrane irritation and other side effects which would be present when using a formulation of highly acidic pH such as described in the prior art.

A stabilizer may be included in the present formulation but, and importantly, is not needed. If included, however, a stabilizer useful in the practice of the present invention is a carbohydrate or a polyhydric alcohol or a chelating agent. A suitable carbohydrate or polyhydric alcohol useful in practice of the present invention is about 1 to 10% (w/v) of a pharmaceutical composition. A suitable chelating agent is approximately 0.04 to 0.2% of the pharmaceutical formulation.

The polyhydric alcohols and carbohydrates share the same chemical feature, i.e., —CHOH—CHOH—, which is responsible for stabilizing peptides and proteins. The polyhydric alcohols include such compounds as sorbitol, mannitol, glycerol, inositol, xylitol, and polypropylene/ethylene glycol copolymer, as well a various polyethylene glycols (PEGs) of molecular weight 200, 400, 1450, 3350, 4000, 6000, and 8000. These molecules are straight chain molecules. The carbohydrate, such as mannose, ribose, trehalose, maltose inositol, erythritol and lactose are cyclic molecules which may contain a keto or aldehyde group. These two classes of compounds have been demonstrated to be effective in stabilizing peptides and proteins against denaturation caused by elevated temperatures and by freeze-thaw or freeze-drying processes and against degradation.

A chelating agent used in practice is EDTA (ethylenediaminetetraacetate) and derivatives. It is a stabilizer used in drugs and cosmetics to prevent ingredients in a given formula from binding with trace elements (particularly minerals) that can exist in water and other ingredients to cause unwanted product changes such as texture, odor, and consistency problems. In particular, it has been shown that trace amounts of heavy metals accelerate the natural hydrolysis of peptides and proteins. Sorbitol and mannitol are the preferred polyhydric alcohols. Another useful feature of the polyhydric alcohols is the maintenance of the tonicity of the lyophilized formulations described herein.

The United States Pharmacopoeia (USP) states that antimicrobial agents in bacteriostatic and fungistatic concentration must be added to preparations contained in multiple dose containers. They must be present in adequate concentration at the time of use to prevent the multiplication of microorganisms inadvertently introduced into the preparation while withdrawing a portion of the content with a hypodermic needle and syringe, or using other invasive means for delivery, such a pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular agent will be effective in one formulation but not effective in another formulation.

A preservative is, in the common pharmaceutical sense, a substance that prevents or inhibits microbial growth and may be added to pharmaceutical formulation for this purpose to avoid consequent spoilage of the formulation by microorganisms. While the amount of the preservative is not large, it may nevertheless affect the overall stability of the peptide, thus even selection of preservative can be difficult.

While the preservative for use in the practice of the present invention can range from 0.005 to 1% (w/v), the preferred range for each preservative, alone or in combination with other is benzyl alcohol (0.2-1%), or m-cresol (0.1-0.3%, or phenol (0.1-0.8%) or combination of methyl (0.05-0.25%) and ethyl or propyl or butyl (0.005%-00.3%) parabens. The parabens are lower alkyl esters of parahydroxybenzoic acid.

A detailed description of each preservative is set forth in "Remington's Pharmaceutical Sciences" as well as Pharmaceutical Dosage Forms: Parenteral Medications, Vol. 1, 1992, Avis et al.

Aviptadil has a tendency to adsorb onto the glass in a glass container when in liquid formulation, therefore, a surfactant can further stabilize the pharmaceutical formulation. Surfactants frequently cause denaturation of protein, both by hydrophilic disruption and by salt bridge separation. Relatively low concentrations of surfactants exert potent denaturing activity, because of the strong interactions between surfactant moieties and the reactive sites on proteins. However, judicious use of this interaction can stabilize peptides and proteins against interfacial or surface denaturation and absorption. Surfactant which could further stabilize the peptide may optionally be present in the range of about 0.001 to 0.3% (w/v) of the total formulation and include poly sorbate 80 (i.e., polyoxyethylene (20) sorbitan monooleate; Tween 80), CHAPS® (i.e., 3-[(3-cholamidopropyl)dimethylammonio] 1-propansulfonate), Brij® (e.g., Brij 35, which is (polyoxyethylene (23) lauryl ether), poloxamer, or another non-ionic surfactant.

It is preferred that the Aviptadil formulation is substantially isotonic. Therefore, it may also be desirable to add sodium chloride or other salt to adjust the tonicity of the pharmaceutical formulation, depending on the tonicifier selected. However, this is optional and depends in the particular formulation selected.

It is also possible that other ingredients may be present in the peptide pharmaceutical formulation of the present invention. Such additional ingredients may include wetting agents, emulsifiers, bulking agents, tonicity modifier, metal ions, oleaginous vehicles, proteins (e.g. human serum albumin, gelatin) and zwitterions (e.g. an amino acid such as betaine, taurine, arginine, glycine, lysine and histidine). Such additional ingredients, of course should not adversely affect the overall stability of the pharmaceutical formulation of the present invention.

The vehicle of greatest importance for parenteral drugs and drugs for inhalation is water. The water of suitable quality for inhaled administration must be prepared either by distillation or by reverse osmosis. Only by these means is it possible to separate adequately various liquid, gas and solid contaminating substances from water. Water for injection is the preferred aqueous vehicle for use in the pharmaceutical formulation of the present invention.

Containers are also an integral part of the formulation of an inhalation or injection and may be considered a component, for there is no container that is totally insoluble or does not in some way affect the liquid it contains, particularly if the liquid is aqueous. Therefore, the selection of a container for an inhaled or parenteral pharmaceutical formulation must be based on a consideration of the composition of the container, as well as of the solution, and the treatment to which it will be subjected. Adsorption of the peptide to the glass surface of the vial can also be minimized by use of borosilicate glass, for example FIOLAX® o.c.-Klar glass (Schott, Germany), Wheaton-33® low extractable borosilicate glass (Wheaton Glass Co., USA) or Corning® Pyrex® 7740 (Corning Inc., USA). Other glass types which can be used e.g. colorless glass, hydrolytic class I plus; 6 R according to DIN ISO 8362 (Schott, St. Gallen, Switzerland), are supposed to meet the criteria of type I borosilicate glass of ASTM (American Society for Testing and Materials), EP (European Pharmacopoeia), and USP (United States Pharmacopoeia). For example, the biological and chemical properties of Aviptadil is stabilized by formulation and lyophilization in a FIOLAX® o.c.-Klar borosilicate glass vial to a final concentration of 0.033 mg/mL and 2 mg/mL of Aviptadil in the presence of 5% mannitol and 0.02% Tween 80.

Stoppers for glass vials, such as, Teflon coated rubber stopper 20 mm, FM259/0 dark grey (Ph.Eur. type I) (Helvoet Pharma, Alken, Belgium) or red injection rubber stoppers 20 mm V9034, (Helvoet Pharma, Alken, Belgium) or any equivalent stopper can be used as the closure for pharmaceutical formulation for inhalation or injection. These stoppers are compatible with Aviptadil as well as with other components of the formulations.

Each of the components of the pharmaceutical formulation described above is known in the art and is described in Pharmaceutical Dosage Forms: Parenteral Medications, Vol. 1, $2^{nd}$ ed., Avis et al. Ed., Marcel Dekker, New York, N.Y. 1992, which is incorporated by reference in its entirety herein.

Any sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, betapropiolactone, ozone, chloropierin, peracetic acid methyl bromide and the like), radiant exposure and aseptic handling. Filtration is the preferred method of sterilization in the practice of the present invention. The sterile filtration involves filtration through 0.22 µm filter. After filtration, the solution is filled into appropriate vials as described above.

The Aviptadil formulation of the present invention may also be lyophilized (freeze-dried). The lyophilized product can then be rehydrated before use.

The formulation of the present invention is preferably intended for inhaled administration. Other possible routes of administration include intramuscular, intravenous, intracavernous, subcutaneous, intradermal, intraarticular, intrathecal, mucosal and the like.

The current invention describes the process and methods for manufacturing of a liquid pharmaceutical composition containing Aviptadil comprising the following steps:
1. Generation of a buffer system which is capable of maintaining the pH value between 4.8 and 6.7 in the absence of a pharmaceutically active amount of Aviptadil and at least one stabilizer
2. Addition of a pharmaceutically active amount of Aviptadil and at least one stabilizer to such buffer.

Preferably, the buffer is an aqueous, or mostly aqueous buffer. The term "mostly aqueous" means that organic solvents can be added up to 15% per volume, preferably up to 10% per volume of the aqueous buffer. Suitable organic solvents are ethanol and/or isopropanol. Further it was found to be advantageous to add at least one stabilizer to the solution containing Aviptadil. Particularly useful stabilizers comprise EDTA and/or mannitol or sorbitol.

The liquid pharmaceutical composition can comprise in addition to Aviptadil a pharmacologically active amount of Cyclo(D-Asp-Pro-D-Val-Leu-D-Trp) and/or Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Lys-Val-Leu-Arg-Arg-His (SEQ ID NO: 2).

The disclosed buffers of the current invention are capable to maintain the pH value constant for at least 4 weeks, preferably at least 6 weeks, more preferably at least 10 weeks, even more preferably one year, particularly preferably for two years, and most preferably for three years. During these time periods the pH value is maintained between 4.8 and 6.7, preferably between 5.0 and 6.4, more preferably between 5.5 and 6.3, most preferably between 5.7 and 6.1, particularly preferably between 5.9 and 6.1.

The liquid pharmaceutical compositions according to the current invention are suitable for the manufacturing of a medicament for the prophylaxis and/or treatment of pulmonary arterial hypertension (PAH), comprising idiopathic pulmonary arterial hypertension, familial pulmonary arterial hypertension, collagen vascular diseases (e.g. scleroderma, lupus erythematosus) associated pulmonary hypertension, congenital systemic-to-pulmonary shunts (large, small, repaired or non-repaired) associated pulmonary hypertension, portal hypertension associated pulmonary hypertension, HIV infection associated pulmonary hypertension, drugs (e.g. anorexigens) and toxins associated pulmonary hypertension, glycogen storage disease associated pulmonary hypertension, Gaucher disease associated pulmonary hypertension, hereditary hemorrhagic telangiectasia associated pulmonary hypertension, hemoglobinopathies associated pulmonary hypertension, myeloproliferative disorders associated pulmonary hypertension, pulmonary veno-occlusive disease associated pulmonary hypertension, pulmonary capillary hemangiomatosis associated pulmonary hypertension, and persistent pulmonary hypertension of the newborn.

The liquid pharmaceutical compositions according to the current invention are suitable for the manufacturing of a medicament for the prophylaxis and/or treatment of left heart diseases associated pulmonary hypertension comprising left-sided atrial or ventricular heart disease associated pulmonary hypertension, and left-sided valvular heart disease associated pulmonary hypertension.

The liquid pharmaceutical compositions according to the current invention are suitable for the manufacturing of a medicament for the prophylaxis and/or treatment of chronic lung diseases and/or hypoxia associated pulmonary hypertension comprising pulmonary hypertension associated with chronic obstructive pulmonary disease (COPD), pulmonary hypertension associated with interstitial lung diseases, pulmonary hypertension associated with sleep disordered-breathing, pulmonary hypertension associated with alveolar hypoventilation disorders, pulmonary hypertension associated with chronic exposure to high altitude, and pulmonary hypertension associated with developmental abnormalities.

The liquid pharmaceutical compositions according to the current invention are suitable for the manufacturing of a medicament for the prophylaxis and/or treatment of chronic thrombotic and/or embolic associated pulmonary hypertension comprising pulmonary hypertension due to chronic thrombotic and/or embolic diseases (e.g. thromboembolic obstruction of proximal pulmonary arteries; thromboembolic obstruction of distal pulmonary arteries); pulmonary embolism due to tumor, parasites, foreign material, pulmonary hypertension associated with in situ thrombosis.

The liquid pharmaceutical compositions according to the current invention are suitable for the manufacturing of a medicament for the prophylaxis and/or treatment of miscellaneous diseases associated with pulmonary hypertension comprising pulmonary hypertension associated with sarcoidosis, pulmonary hypertension associated with histiocytosis X, pulmonary hypertension associated with lymphangiomatosis, pulmonary hypertension associated with sickle-cell disease, Eisenmenger syndrome, and chronic fatigue syndrome.

The liquid pharmaceutical compositions according to the current invention are suitable for the manufacturing of a medicament for the prophylaxis and/or treatment of autoimmune diseases comprising bronchial asthma, rheumatoid arthritis, lupus, scleroderma, Sjogren's syndrome, Goodpasture's syndrome, Wegener's granulomatosis, type I diabetes mellitus, Hashimoto's thyroiditis, Grave's disease, multiple sclerosis, Guillain-Barre syndrome, Addison's disease, acute disseminated encephalomyelitis, antiphospholipid antibody syndrome, aplastic anemia, myasthenia gravis, opsoclonus myoclonus syndrome, optic neuritis, Ord's thyroiditis, and sarcoidosis.

The liquid pharmaceutical compositions according to the current invention are suitable for the manufacturing of a medicament for the prophylaxis and/or treatment of acute respiratory distress syndrome, and acute lung injury.

The liquid pharmaceutical compositions according to the current invention are suitable for the manufacturing of a medicament for the prophylaxis and/or treatment of chronic obstructive pulmonary disease (COPD).

The liquid pharmaceutical compositions according to the current invention are suitable for the manufacturing of a medicament for the prophylaxis and/or treatment of interstitial lung diseases (ILDs) comprising Hamman-Rich syndrome, idiopathic pulmonary fibrosis, bronchiolitis obliterans, hypersensitivity pneumonitis, lymphangiomyomatosis (LAM), usual interstitial pneumonia (UIP), Von Gierke Syndrome and Osler-Weber-Rendu-Syndrome.

The liquid pharmaceutical compositions according to the current invention are suitable for the manufacturing of a medicament for the prophylaxis and/or treatment of central nervous system disorders comprising Parkinson's disease and Alzheimer's disease The liquid pharmaceutical compositions according to the current invention are suitable for the manufacturing of a medicament for the prophylaxis and/or treatment of small cell lung carcinoma.

The medicaments of the invention are preferentially formulated for inhalative or injectable administration. Suitable protocols for the administration of the inventive Aviptadil formulations are presented in Examples 6 and 7 below.

Furthermore, the preferred soluble pharmaceutical compositions are prepared in a sterile form.

Long term stability studies demonstrated that the disclosed liquid pharmaceutical compositions and medicaments are stable for longer than formulations in the prior art.

The invention will now be described in greater detail by reference to the following non-limiting examples.

Formulations of the invention are generally described above. Examples of various formulations useful in the invention are provided. These examples are not limited to the invention and those of ordinary skill in the art can readily construct other formulations within the ambit of the claims.

EXAMPLES

In the following examples the stability of the different Aviptadil formulations were assessed by determining the purity of Aviptadil and assay (quantity) of Aviptadil by HPLC.

The major degradation pathway of Aviptadil is peptide bond hydrolysis. A major loss in assay (quantity) also occurs due to the adherence on the glass vials.

In all examples the test sample was compared to a reference sample which was the same sample measured at day zero. Thus, the % loss in purity and % loss in assay for all test samples are expressed as a percentage difference from the reference sample purity value or reference sample assay value at day zero.

For all the tested formulations below the appearance of the pharmaceutical compositions after storage times was clear and colorless.

Example 1

The stability of the Aviptadil was investigated in the pH range of 5 to 7 at the temperature and for the length of time indicated in the Tables 1-4 below.

The pH versus purity and assay profile for the peptide in 150 mM citrate buffer and 1 mM EDTA is shown in Table 1 and for the peptide in 150 mM acetate buffer is shown in Table 2 and for the peptide in 150 mM phosphate buffer is shown in Tables 3 and 4.

TABLE 1

| 25° C. (closed) for 13 days | | | | |
|---|---|---|---|---|
| 0.15 M citric acid/trisodium citrate buffer/1 mM EDTA | pH | 5.0 | 6.0 | 7.0 |
| | % Loss in Purity | −3.0 | −0.1 | −17.1 |
| | % Loss in Assay | −15.2 | −11.9 | −28.4 |

TABLE 2

| 25° C. (closed) for 14 days | | | | | |
|---|---|---|---|---|---|
| 0.15 M acetic acid/sodium acetate buffer | pH | 4.0 | 5.0 | 6.0 | 7.0 |
| | % Loss in Purity | −11.3 | −6.3 | −1.67 | −6.15 |
| | % Loss in Assay | −14.8 | −11.3 | −8.41 | −15.21 |

TABLE 3

| 2-8° C. (closed) for 31 days | | | | |
|---|---|---|---|---|
| 0.15 M phosphoric acid/trisodium phosphate buffer | pH | 5.0 | 6.0 | 7.0 |
| | % Loss in Purity | −1.7 | +1.2 | −2.7 |
| | % Loss in Assay | −5.5 | −3.3 | −8.7 |

TABLE 4

| 25° C. (closed) for 13 days and 2-8° C. for 18 days | | | | |
|---|---|---|---|---|
| 0.15 M phosphoric acid/trisodium phosphate buffer | pH | 5.0 | 6.0 | 7.0 |
| | % Loss in Purity | −8.1 | −4.7 | −23.5 |
| | % Loss in Assay | −17.3 | −12.4 | −31.8 |

It can be observed from these tables that Aviptadil is most stable at about pH 6. The FIG. 1 summarizes the Loss in Purity data presented in the above tables to more clearly demonstrate the improved stability of Aviptadil at about pH 6.

Example 2

This example describes a liquid formulation for Aviptadil using citrate buffer or 0.9% sodium chloride without buffer component. The pH of the sodium chloride solution was between 5.3 and 5.8. Solutions having a pH value of about 6 have been shown to increase the stability of Aviptadil (see Example 1).

Another important feature of the formulation is the amount of Aviptadil within the solution. Surprisingly, the inventors found that formulations containing Aviptadil amounts of from 0.0066% to 0.2% Aviptadil were more stable than formulation containing less than 0.0066% Aviptadil, as measured by % loss in assay (see table 5). The purity of sample did not show any significant change at the different concentrations of Aviptadil. The shelf life increased about 3-fold when the Aviptadil concentration was increased from 0.033 mg/mL to 0.066 mg/mL.

TABLE 5

| | Aviptadil concentration | 0.033 mg/mL | 0.066 mg/mL | 2 mg/mL |
|---|---|---|---|---|
| 0.15 M sodium chloride at 2-8° C. for 10 weeks | % Loss in Assay | −7.9 | −2.7 | −1.7 |
| 0.12 M citrate buffer, pH 5.7 at 2-8° C. for 10 weeks | % Loss in Assay | −6.5 | +1.15 | Not tested |

Example 3

Based on the finding that Aviptadil was most stable at a pH of about 6 and with an amount of about 0.0066% Aviptadil, the following formulations were developed:

| Formulation A | |
|---|---|
| INGREDIENT | Weight % (w/v) |
| Aviptadil base | 0.0066-0.5 |
| Sodium chloride | 0.9 |
| Water For Injection | 100 mL |

In formulation B mannitol is added to the formulation to increase the stability of Aviptadil.

| Formulation B | |
|---|---|
| INGREDIENT | Weight % (w/v) |
| Aviptadil | 0.0066-1.0 |
| Mannitol | 4.0 |
| Sodium chloride | 0.16 |
| Water For Injection | 100 mL |

| Formulation C | |
|---|---|
| INGREDIENT | Weight % (w/v) |
| Aviptadil | 0.001-1.0 |
| Citrate buffer (50 mM, pH 5.8) | |
| Citric acid | 0.227 |
| Trisodium citrate dihydrate | 1.12 |
| Mannitol | 4.0 |
| Water For Injection | 100 mL |

Formulation D

| INGREDIENT | Weight % (w/v) |
| --- | --- |
| Aviptadil | 0.001-1.0 |
| Citrate buffer (120 mM, pH 5.7) | |
| Citric acid | 0.59 |
| Trisodium citrate dihydrate | 2.62 |
| EDTA trisodium tetrahydrate | 0.23 |
| Water For Injection | 100 mL |

The above formulation D with 0.003 and 0.2% Aviptadil was intratracheally administered to the lung of rats. No irritancy of the lung or trachea was noted. The histomorphological examination of the lungs and trachea did not reveal any morphological changes related to this Aviptadil formulation.

The stability of the above formulation with 0.0033% Aviptadil substance was evaluated at 5° C. and 25° C. Assay and purity of Aviptadil were determined by HPLC. Approximately 15% loss in assay and 7% loss in purity were considered acceptable. The shelf-life of the pharmaceutical formulation at 25° C. based on direct measurement is at least 27 days (see Table 6).

TABLE 6

| 0.15 M citric acid/trisodium citrate buffer at 25° C. for 27 days | % Loss in assay | −12 |
| --- | --- | --- |
| | % Loss in Purity | −3 |

When stored at 5° C. the shelf-life of the pharmaceutical formulation based on direct measurement is at least 9 months (see Table 7).

TABLE 7

| 0.15 M citric acid/trisodium citrate buffer, 1 mM EDTA at 5° C. for 37 weeks | % Loss in assay | −14 |
| --- | --- | --- |
| | % Loss in Purity | −3 |

As shown in Example 2 higher concentrations of Aviptadil are more stable. The above formulation with 0.0033% drug showed a loss in assay of about 4.4% after 10 weeks storage at 5° C., whereas formulation with 0.0066% drug showed no loss at all. By extrapolation of these data shelf life of at least 2 years for Aviptadil was predicted.

Citrate can also be replaced by acetate in the formulation.

Formulation E

| INGREDIENT | Weight % (w/v) |
| --- | --- |
| Aviptadil | 0.001-1.0 |
| Acetate buffer (30 mM, pH 5.7) | |
| Sodium acetate trihydrate | 0.732 |
| Glacial acetic acid | 0.0371 |
| mannitol | 4.3 |
| Water For Injection | 100 mL |

Citrate can also be replaced by phosphate in the formulation.

Formulation F

| INGREDIENT | Weight % (w/v) |
| --- | --- |
| Aviptadil | 0.001-1.0 |
| Phosphate buffer (50 mM, pH 6.0) | |
| Sodium hydrogen phosphate | 0.0422 |
| Sodium dihydrogen phosphate monohydrate | 0.649 |
| Sodium chloride | 0.4 |
| Polysorbate 80 | 0.02 |
| Water For Injection | 100 mL |

Formulation G

| INGREDIENT | Weight % (w/v) |
| --- | --- |
| Aviptadil | 0.001-1.0 |
| Phosphate buffer (20 mM, pH 5.8) | |
| Sodium hydrogen phosphate | 0.023 |
| Sodium dihydrogen phosphate monohydrate | 0.254 |
| Mannitol | 4.2 |
| Polysorbate 80 | 0.02 |
| Water For Injection | 100 mL |

Example 4

The Addition of a Surfactant can Reduce the Absorbance of Aviptadil to the Surface of Glass Vials

Formulation H

| INGREDIENT | Weight % (w/v) |
| --- | --- |
| Aviptadil | 0.001-1.0 |
| Acetate buffer (12 mM, pH 5.9) | |
| Sodium acetate trihydrate | 0.308 |
| Glacial acetic acid | 0.008 |
| mannitol | 4.4 |
| Polysorbate 80 | 0.02 |

-continued

Formulation H

| INGREDIENT | Weight % (w/v) |
| --- | --- |
| m-cresol | 0.225 |
| Water For Injection | 100 mL |

Formulation I

| INGREDIENT | Weight (%) |
| --- | --- |
| Aviptadil | 0.0066-1.0 |
| Sodium chloride | 0.15% |
| mannitol | 4.1 |
| Polysorbate 80 | 0.02 |
| m-cresol | 0.3 |
| Water For Injection | 100 mL |

Example 5

The liquid pharmaceutical formulations can also be lyophilized. The shelf-life of the lyophilized formulation was at least 1 year at 25° C. Aviptadil can also be minimal formulated with mannitol or with mannose.

Formulation J

| INGREDIENT | Weight (%) |
| --- | --- |
| Aviptadil | 0.001-1.0 |
| mannitol | 5.0 |
| Water For Injection | 100 mL |

Example 6

The following provides clinical examples for drug dosages, safety and efficacy for inhaled administration by chronically ill patients of the medicament formulation at pH values between 5.3-6.0.

Post-VSD

A patient suffering from pulmonary hypertension associated to post-ventricular septal defect (post-VSD) inhaled 100 micrograms of Aviptadil as a single dose without any irritation of the lungs. The efficacy of the medicament is demonstrated by a decrease of 21% in pulmonary vascular resistance consisting of an increase of cardiac output and decrease of mean arterial pulmonary pressure, while having no systemic side effects, and as compared to the patient's baseline characteristics. The daily dose for that patient comprises 400 micrograms split into 4 single dosages of 100 micrograms of Aviptadil each. Thus a weekly dosage for such a patient is 2800 micrograms Aviptadil.

IPAH

A patient suffering from idiopathic pulmonary arterial hypertension (IPAH) inhaled 100 micrograms of Aviptadil as a single dose without any irritation of the lungs. The efficacy of the medicament is demonstrated by a decrease of 20% in pulmonary vascular resistance consisting of an increase of cardiac output and decrease of mean arterial pulmonary pressure, while having no systemic side effects, and as compared to the patient's baseline characteristics. The daily dose for that patient comprises 400 micrograms in 4 single dosages of 100 micrograms of Aviptadil each. Thus a weekly dosage for such a patient is 2800 micrograms Aviptadil.

CREST Syndrome

A patient suffering from pulmonary hypertension associated to scleroderma (CREST syndrome—Calcinosis; Raynaud's disease; loss of muscle control of the Esophagus; Sclerodactyly; Telangiectasia) inhaled 100 micrograms of Aviptadil as a single dose without any irritation of the lungs. The efficacy of the medicament is demonstrated by a decrease of 14% in pulmonary vascular resistance mainly consisting of an increase of cardiac output, while having no systemic side effects, and as compared to the patient's baseline characteristics. The daily dose for that patient comprises 400 micrograms split in 4 single dosages of 100 micrograms of Aviptadil each. Thus a weekly dosage for such a patient is 2800 micrograms Aviptadil.

Extrinsic Allergic Alveolitis

A patient suffering from pulmonary hypertension associated with extrinsic allergic alveolitis inhaled 100 micrograms of Aviptadil as a single dose without any irritation of the lungs. The efficacy of the medicament is demonstrated by a decrease of 21% in pulmonary vascular resistance consisting of an increase of cardiac output and decrease of mean arterial pulmonary pressure, while having no systemic side effects, and as compared to the patient's baseline characteristics. The daily dose for that patient comprises 400 micrograms in 4 single dosages of 100 micrograms of Aviptadil each. Thus a weekly dosage for such a patient is 2800 micrograms Aviptadil.

Chronic Obstructive Pulmonary Disease

A patient suffering from pulmonary hypertension associated to chronic obstructive pulmonary disease inhaled 100 micrograms of Aviptadil as a single dose without any irritation of the lungs. The efficacy of the medicament is demonstrated by a decrease of 20% in pulmonary vascular resistance consisting of an decrease of mean arterial pulmonary pressure, while having no systemic side effects, and as compared to the patient's baseline characteristics. The daily dose for that patient comprises 400 micrograms in 4 single dosages of 100 micrograms of Aviptadil each. Thus a weekly dosage for such a patient is 2800 micrograms Aviptadil.

A patient suffering from pulmonary hypertension associated to chronic obstructive pulmonary disease inhaled 200 micrograms of Aviptadil as a single dose without any irritation of the lungs. The efficacy of the medicament is demonstrated by a decrease of 25% in pulmonary vascular resistance consisting of an increase of cardiac output and decrease of mean arterial pulmonary pressure, while having no systemic side effects, and as compared to the patient's baseline characteristics. The daily dose for that patient comprises 800 micrograms in 4 single dosages of 200 micrograms of Aviptadil each. Thus a weekly dosage for such a patient is 5600 micrograms Aviptadil.

Example 7

The following provides clinical examples for drug dosages, safety and efficacy for infused administration of the medicament formulation at pH values between 5.3-6.0 for patients with acute life threatening conditions like respiratory distress syndrome due to sepsis, burns, gas intoxications, and ischemia.

Acute Respiratory Distress Syndrome

A patient suffering from acute respiratory distress syndrome received the following doses of Aviptadil via intravenous infusion: 50 pmol Aviptadil/kg bodyweight/hr for 12 hrs, and since the patient weighed 71 kg (rounded up to 75 kg), the patient received 3,750 pmol Aviptadil/hr. This equals 150 micrograms of Aviptadil over the 12 hr infusion, or 12.5 µg Aviptadil/hr of infusion. The patient had no systemic side effects, survived and was discharged from intensive care unit and hospital.

Acute Respiratory Distress Syndrome Due to Sepsis from Peritonitis

A patient suffering from acute respiratory distress syndrome due to sepsis from peritonitis received the following dose of Aviptadil via intravenous infusion: 50 pmol Aviptadil/kg bodyweight/hr for 12 hrs, and since the patient weighed 63 kg (rounded up to 65 kg), the patient receive 3,250 pmol Aviptadil/hr. This equals 130 micrograms of Aviptadil over the 12 hr infusion, or 10.8 µg Aviptadil/hr of infusion. The patient had no systemic side effects, survived and was discharged from intensive care unit and hospital for rehabilitation.

Due to the proven safety, the infused administration of Aviptadil is easily extendable for 24 hours and 36 hours at: 50 pmol Aviptadil/kg bodyweight/hr.

DESCRIPTION OF FIGURE

The FIGURE shows the stability of Aviptadil which depends on pH of the buffer solution. The FIGURE exhibits the % loss in purity of Aviptadil for all test samples of example 1 as a percentage difference from the reference sample purity value at day zero.

The invention claimed is:

1. A liquid, pharmaceutical formulation comprising 0.001 to 1.0% (w/v) Aviptadil in a buffer, wherein said buffer maintains the pH of the formulation at a pH of 4.8 to 6.7.

2. The liquid, pharmaceutical formulation of claim 1 which is substantially isotonic.

3. The liquid, pharmaceutical formulation of claim 2 which further comprises as stabilizer about 1% to about 10% a carbohydrate or a polyhydric alcohol.

4. The liquid, pharmaceutical formulation of claim 2 which further comprises a preservative.

5. The liquid, pharmaceutical formulation of claim 1 wherein said buffer is selected from the group of formate, lactate, benzoic acid, oxalate, fumarate, aniline, acetate buffer, citrate buffer, glutamate buffer, phosphate buffer, succinate, pyridine, phthalate, histidine, 2-(N-morpholino) ethanesulphonic acid; maleic acid, cacodylate, carbonic acid, N-(2-acetamido)imino-diacetic acid, 4-piperazinebis-(ethanesulfonic acid), BIS-TRIS-Propane, ethylendiamine, 2-[(2-amino-2-oxoethyl)amino]ethanesulphonic acid, imidazole, 3-(N-morphin)-propansulfonic acid, Diethylmalonic acid, 2-[tris (hydroxymethyl)methyl amino ethanesulphonic acid; and N-2-hydroxylethylpiperazin-N'-2-ethansulfonic acid.

6. The liquid, pharmaceutical formulation of claim 1 wherein the pharmaceutical formulation comprises about 0.0066% to 1.0% (w/v) Aviptadil.

7. The liquid, pharmaceutical formulation of claim 1 wherein said buffer is an acetate buffer or a citrate buffer.

8. The liquid, pharmaceutical formulation of claim 1 wherein the pH of said formulation is in the range of 5.0 to 6.4.

9. The liquid, pharmaceutical formulation of claim 8 wherein the pH of said formulation is in the range of 5.7 to 6.1.

10. The liquid, pharmaceutical formulation of claim 1 wherein the pKa of said buffer is in the range of 3.8 to 7.7.

11. The liquid, pharmaceutical formulation of claim 10 wherein the pKa of said buffer is in the range of 4.5 to 7.3.

12. The liquid, pharmaceutical formulation of claim 3 wherein the polyhydric alcohol is selected from the group consisting of sorbitol, mannitol, glycerol, inositol, xylitol, polypropylene/ethylene glycol copolymer, PEG 200, PEG 400, PEG 1450, PEG 3350, PEG 4000, PEG 6000, and PEG 8000.

13. The liquid, pharmaceutical formulation of claim 3 wherein the carbohydrate is selected from the group consisting of mannose, ribose, trehalose, maltose, inositol, erythritol and lactose.

14. The liquid, pharmaceutical formulation of claim 4 wherein the preservative is selected from the group consisting of benzyl alcohol, m-cresol, phenol paraben, methyl paraben, ethyl paraben, propyl paraben, butyl paraben and phenol.

15. The liquid, pharmaceutical formulation of claim 14 wherein the preservative is approximately about 0.1% (w/v) to about 0.3% (w/v) cresol.

16. The liquid, pharmaceutical formulation of claim 1, wherein said formulation further comprises a surfactant.

17. The liquid, pharmaceutical formulation of claim 16, wherein said surfactant is selected from the group consisting of polysorbate 80 (polyoxyethylene(20) sorbitan monooleate), 3-[3-chloamidopropyl)dimethylammonio] 1-propansulfonate, polyoxyethylene(23) lauryl ether, poloxamer and a non-ionic surfactant.

18. The liquid, pharmaceutical formulation of claim 17, wherein said surfactant is 0.02% (w/v) polysorbate 80.

19. The liquid, pharmaceutical formulation of claim 1, wherein said formulation further comprises the pharmacological active peptide Cyclo(D-Asp-Pro-D-Val-Leu-D-Trp) and/or Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Lys-Val-Leu-Arg-Arg-His (SEQ ID NO:2).

20. The lyophilized product of the liquid pharmaceutical formulation of claim 1.

* * * * *